United States Patent [19]

Carson et al.

[11] Patent Number: 4,937,371

[45] Date of Patent: Jun. 26, 1990

[54] DIHYDROXYNAPHTHALENE DERIVATIVES

[75] Inventors: Mathew Carson, Nutley; Ru-Jen L. Han, Princeton Junction; Ronald A. LeMahieu, North Caldwell, all of N.J.

[73] Assignee: Hoffmann-La Roche Inc., Nutley, N.J.

[21] Appl. No.: 422,095

[22] Filed: Oct. 20, 1989

Related U.S. Application Data

[63] Continuation-in-part of Ser. No. 313,117, Feb. 21, 1989, abandoned.

[51] Int. Cl.$^5$ ............................................. C07C 69/76
[52] U.S. Cl. ..................................... 560/53; 560/56; 562/462; 562/466
[58] Field of Search .................. 560/53, 56; 562/462, 562/466

[56] References Cited

U.S. PATENT DOCUMENTS

| | | | |
|---|---|---|---|
| 4,351,950 | 9/1982 | Sircar | 560/56 |
| 4,374,262 | 2/1983 | McGinnis | 560/56 |
| 4,391,731 | 7/1983 | Bollen et al. | 560/56 |

FOREIGN PATENT DOCUMENTS

| | | |
|---|---|---|
| 2251556 | 4/1973 | Fed. Rep. of Germany . |
| 2258366 | 9/1975 | France . |

Primary Examiner—Paul J. Killos
Attorney, Agent, or Firm—George M. Gould; Bernard S. Leon; A. Kate Huffman

[57] ABSTRACT

There are described dihydroxy naphthalene derivatives of the formula

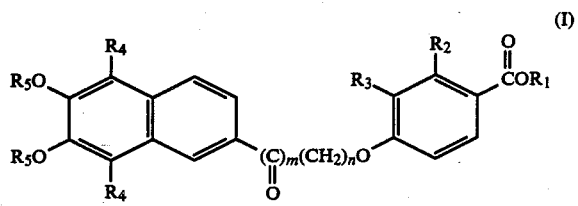

in which $R_1$ is hydrogen, lower alkyl or benzyl, $R_2$ is hydrogen, hydroxy or lower alkanoyloxy, $R_3$ is hydrogen or lower alkyl, $R_4$ is hydrogen or halogen, $R_5$ is hydrogen, acyl, methyl or benzyl, m is 0 or 1, and n is an integer from 2 to 10, as well as salts thereof with pharmaceutically acceptable bases when $R_1$ is hydrogen.

These compounds are useful as agents for the treatment of inflammatory bowel diseases, for instance, colitis, as pro-drugs, or as intermediates for the preparation of such compounds.

22 Claims, No Drawings

DIHYDROXYNAPHTHALENE DERIVATIVES

This is a continuation-in-part of application Ser. No. 07/313,117, filed Feb. 21, 1989, now abandoned.

SUMMARY OF THE INVENTION

This invention concerns derivatives of 6,7-dihydroxynaphthalene, which are of the formula

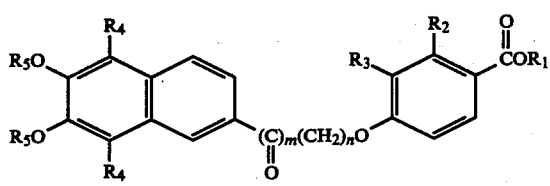

in which $R_1$ is hydrogen, lower alkyl or benzyl, $R_2$ is hydrogen, hydroxy or lower alkanoyloxy, $R_3$ is hydrogen or lower alkyl, $R_4$ is hydrogen or halogen, $R_5$ is hydrogen, acyl, methyl or benzyl, m is 0 or 1, and n is an integer from 2 to 10, as well as, when $R_1$ is hydrogen, salts thereof with pharmaceutically acceptable bases.

The compounds of formula I are useful as agents for the treatment of various inflammatory conditions or diseases of the gastrointestinal tract, including inflammatory bowel disease (IBD), or as intermediates which are chemically convertible to such agents.

In general, those compounds of formula I in which $R_5$ is hydrogen or acyl and $R_1$ is hydrogen are directly active as anti-inflammatory agents and are useful as such. The compounds of formula I in which $R_5$ is hydrogen or acyl and $R_1$ is lower alkyl or benzyl are prodrugs for such agents, i.e., are hydrolyzable to the active form upon administration. Those compounds of formula I in which $R_5$ is methyl or benzyl are useful as intermediates for the formation of the therapeutically active compounds of formula I (i.e., in which $R_5$ is hydrogen or acyl).

DETAILED DESCRIPTION OF THE INVENTION

As used herein, the term "lower alkyl" denotes a straight or branched chain saturated hydrocarbon containing from 1 to 7 carbon atoms, for example, methyl, ethyl, propyl, isopropyl, butyl, t-butyl, neopentyl, pentyl, heptyl, and the like.

The term "halogen" denotes all of the halogens, that is, bromine, chlorine, iodine and fluorine.

The term "acyl" denotes an "alkanoyl" group derived from an aliphatic carboxylic acid of from 1 to 7 carbon atoms, for example, formyl, acetyl, propionyl, and the like, and an "aroyl" group derived from an aromatic carboxylic acid, for example, benzoyl and the like.

The term "alkanoyloxy" denotes a group derived from an aliphatic carboxylic acid of from 1 to 7 carbon atoms, for example, formyloxy, acetoxy, propionyloxy, and the like.

Preferred compounds of formula I of the invention are those in which $R_1$ is hydrogen. $R_2$ is hydroxy. $R_3$ is lower alkyl, $R_4$ and $R_5$ are hydrogen, n is 2-10, and m is 0 or 1.

Most preferred compounds of formula I are those in which $R_1$ is hydrogen, $R_2$ is hydroxy, $R_3$ is propyl, $R_4$ and $R_5$ are hydrogen, n is 4-6 and m is 0.

The most preferred compounds of the invention are the following:
2-Hydroxy-4-[[6-(6,7-dimethoxy-2-naphthalenyl)-6-oxo-hexyl]oxy]3-propylbenzoic acid;
4-[[6-(6,7-Dihydroxy-2-naphthalenyl)-6-oxo-hexyl-]oxy]-2-hydroxy-3-propylbenzoic acid;
2-Hydroxy-4-[6-(6,7-dimethoxy-2-naphthalenyl)hexyloxy]-3-propylbenzoic acid;
4-[6-(6,7-Dihydroxy-2-naphthalenyl)hexyloxy]-2-hydroxy-3-propylbenzoic acid;
2-Hydroxy-4-[4-(6,7-dimethoxy-2-naphthalenyl)-butoxy]-3-propylbenzoic acid;
4-[4-(6,7-Dihydroxy-2-naphthalenyl)butoxy]-2-hydroxy-3-propylbenzoic acid;
4-[6-[6,7-bis(Phenylmethoxy)-2-naphthalenyl]hexyloxy]benzoic acid;
4-[6-(6,7-Dihydroxy-2-naphthalenyl)hexyloxy]benzoic acid;
2-Hydroxy-4-[3-(6,7-dimethoxy-2-naphthalenyl)-propoxy]-3-propylbenzoic acid;
4-[3-(6,7-Dihydroxy-2-naphthalenyl)propoxy]-2-hydroxy-3-propylbenzoic acid;
2-Hydroxy-4-[2-(6,7-dimethoxy-2-naphthalenyl)ethoxy]-3-propylbenzoic acid;
4-[2-(6,7-Dihydroxy-2-naphthalenyl)ethoxy]-2-hydroxy-3-propylbenzoic acid;
2-Hydroxy-4-[6-[6,7-bis(phenylmethoxy)-2-naphthalenyl]-hexyloxy]benzoic acid;
4-[6-(6,7-Dihydroxy-2-naphthalenyl)hexyloxy]-2-hydroxybenzoic acid;
2-Hydroxy-4-[[5-(6,7-dimethoxy-2-naphthalenyl)-5-oxopentyl]oxy]-3-propylbenzoic acid;
4-[[5-(6,7-Dihydroxy-2-naphthalenyl)-5-oxopentyl-]oxy]-2-hydroxy-3-propylbenzoic acid;
2-Hydroxy-4-[5-(6,7-dimethoxy-2-naphthalenyl)pentyloxy]-3propylbenzoic acid;
4-[5-(6,7-Dihydroxy-2-naphthalenyl)pentyloxy]-2-hydroxy-3-propylbenzoic acid;
4-[4-(5,8-Dichloro-6,7-dimethoxy-2-naphthalenyl)-butoxy]-2-hydroxy-3-propylbenzoic acid; and
4-[4-(5,8-Dichloro-6,7-dihydroxy-2-naphthalenyl)-butoxy]-2-hydroxy-3-propylbenzoic acid;

as well as readily hydrolyzable esters and pharmaceutically acceptable salts of any of the foregoing.

The compounds of formula I and intermediates for such compounds can be prepared as described in Reaction Schemes I to V.

REACTION SCHEME I

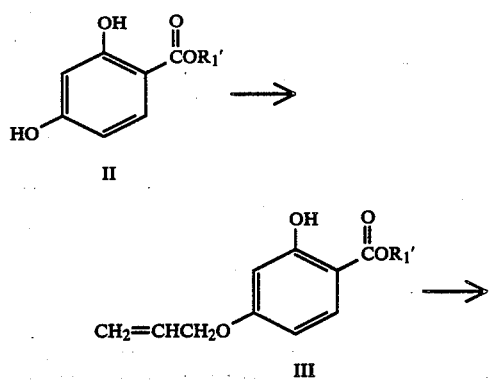

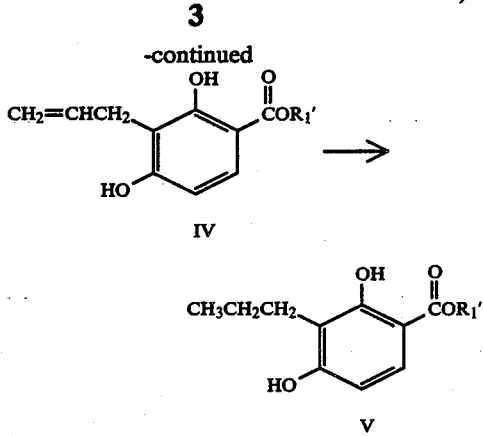

$R_1'$ = lower alkyl

In Reaction Scheme I, a compound of formula II, which is a known compound and is commercially available, can be converted to the corresponding compound of formula III by standard alkylation conditions, for example utilizing allyl bromide or chloride, an alkali metal carbonate such as sodium carbonate or preferably potassium carbonate in a solvent such as methyl ethyl ketone, dimethylformamide, or, preferably, acetone, at a temperature in the range of from about 40° to about 60° C.

The rearrangement of a compound of formula III to a compound of formula IV is carried out by heating in an inert atmosphere at a temperature in the range of from about 175° to about 200° C.

The hydrogenation of a compound of formula IV to the corresponding compound of formula V can be carried out under standard catalytic hydrogenation conditions, for example, at atmospheric pressure or under hydrogen pressure such as 50 psi, in a solvent such as ethyl acetate, tetrahydrofuran, ethanol or the like, at a temperature in the range of from about 25° to about 50° C.

REACTION SCHEME II

In Reaction Scheme II, a compound of formula VI, which is a known compound and commercially available, can be converted to a compound of formula VII utilizing standard acylation conditions, for example, treatment with a haloacid chloride and aluminum chloride in a solvent such as methylene chloride or 1,2-dichloroethane at a temperature in the range of from 0° C. to about 40° C.

The reduction of a compound of formula VII to the corresponding compound of formula VIII can be accomplished by hydrogenation in a Parr apparatus at hydrogen pressures of about 50 to about 60 psi, using a palladium catalyst in a solvent such as ethanol, ethyl acetate, tetrahydrofuran, acetic acid or the like, at a temperature in the range of from 25° C. to about 70° C. A mineral acid catalyst, e.g., sulfuric acid, is used in addition to the palladium catalyst.

The conversion of a compound of formula VIII to a compound of formula IX is accomplished by treatment with boron tribromide in a halogenated hydrocarbon solvent such as 1,2-dichloroethane, or preferably, methylene chloride at a temperature in the range of from about −75° to about 25° C.

The resulting compound of formula IX can be converted to the corresponding compound of formula X by treatment with benzyl chloride or benzyl bromide, potassium iodide or sodium iodide, and an alkali metal carbonate, such as sodium or potassium carbonate, in a solvent such as acetone, methyl ethyl ketone or the like, at reflux or with dimethylformamide, at a temperature of from about 50° C. to about 100° C.

A compound of formula VIII can be converted to a dichloro derivative of formula XI by treatment with sulfuryl chloride in a halogenated hydrocarbon solvent, such as methylene chloride or 1,2-dichloroethane, at a temperature of from about 0° C. to about 30° C.

REACTION SCHEME III

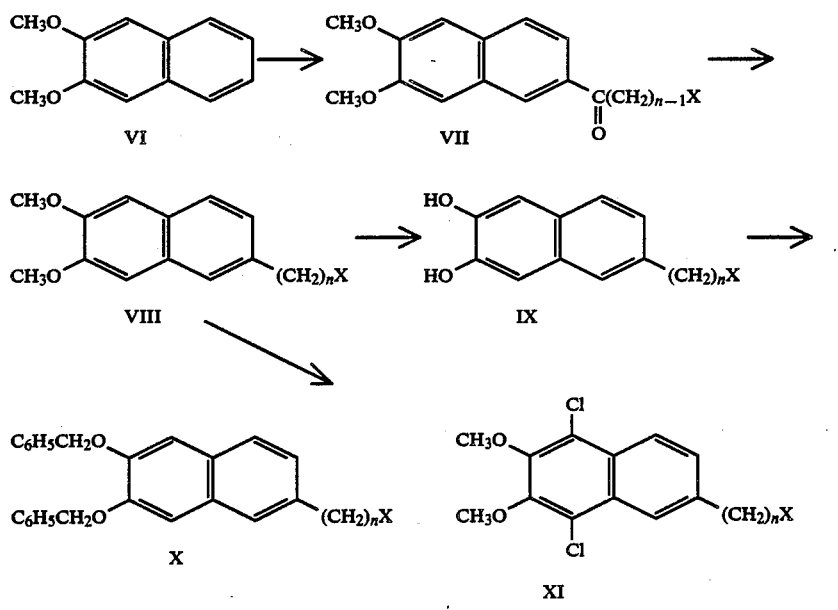

X = halogen and n is as defined previously

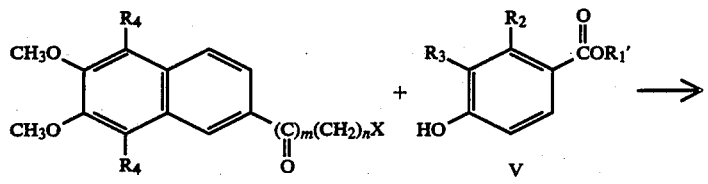

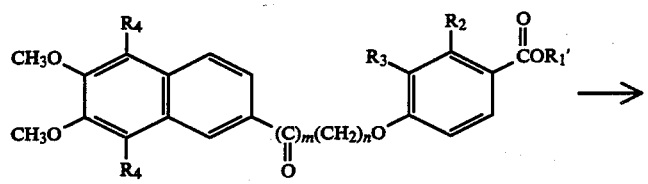

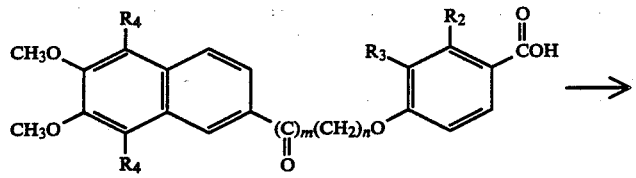

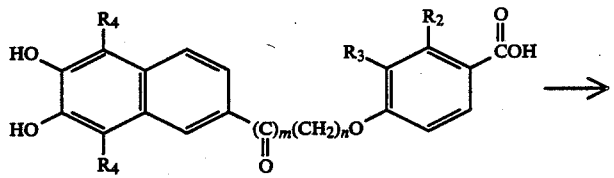

$R_1'$ = lower alkyl If m = 1, then n = 4–9 If m = 0, then n = 2–10 $R_2$, $R_3$ $R_4$ and X are as defined previously In Reaction Scheme III, a compound of formula VII is reacted with a compound of formula V, to yield a compound of formula XII. The reaction is carried out using an alkali metal carbonate as the base, for example, sodium carbonate or, preferably, potassium carbonate, with added sodium iodide or potassium iodide in a solvent such as acetone, methyl ethyl ketone or dimethylformamide, at a temperature in the range of from about 40° C. to about 70° C. The phase transfer catalyst, tris-[2-(2-methoxyethoxy)ethyl]amine (TDA-1), can be used to facilitate the reaction, which is then carried out in a refluxing solvent such as toluene.

The hydrolysis of a compound of formula XII to the corresponding compound of formula XIII can be carried out under standard conditions, for example, utilizing an alkali metal hydroxide, such as sodium or potassium hydroxide in a solvent such as methanol, ethanol or the like, sometimes with added dioxane to facilitate solubility, at a temperature in the range of from about 25° C. to about 65° C.

The conversion of a compound of formula XIII to the corresponding compound of formula Ia can be carried out by treatment with boron tribromide in a solvent such as methylene chloride, 1,2-dichloroethane or the like, at a temperature in the range of from about −70° C. to about 25° C. The resulting compound of formula Ia is recovered and purified by conventional procedures, for example precipitation, crystallization, chromatography or the like.

REACTION SCHEME IV

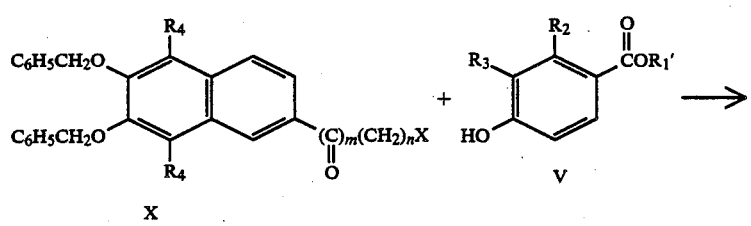

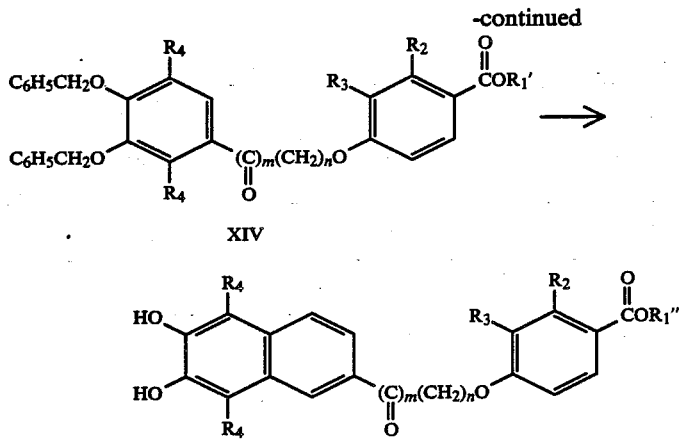

Ib $R_1' = $ lower alkyl or benzyl $R_1'' = $ lower alkyl or hydrogen m and n are as in Scheme III $R_2$, $R_3$, $R_4$ and X are as defined previously In Reaction Scheme IV, a compound of formula X is reacted with a compound of formula V, to yield a compound of formula XIV. The reaction is carried out as described for the first step of Reaction Scheme III.

The benzyl protecting groups can then be removed from the compound of formula XIV by standard hydrogenation conditions, for example, stirring in a hydrogen atmosphere at room temperature (e.g., 23°–25° C.) in the presence of a catalyst such as palladium.

In the case where $R_1$, is benzyl, this results in the compound of formula Ib where $R_1''$ is hydrogen. In the case where $R_1$, is lower alkyl, this results in the compound of formula Ib where $R_1''$ is lower alkyl.

REACTION SCHEME V

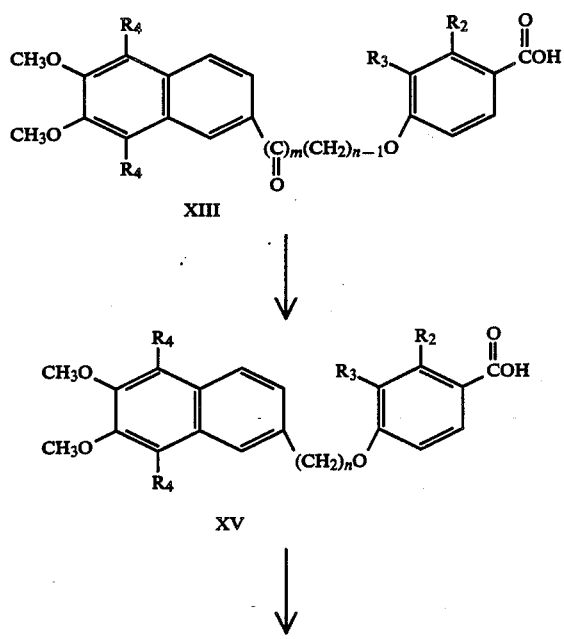

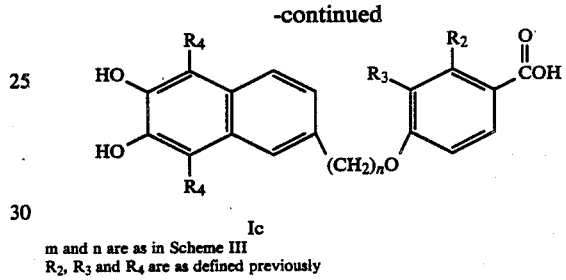

Ic m and n are as in Scheme III
$R_2$, $R_3$ and $R_4$ are as defined previously In Reaction Scheme V, a compound of formula XIII can be converted to the corresponding compound of formula XV by hydrogenation in a Parr apparatus at hydrogen pressures of about 50 to about 60 psi, using a palladium catalyst in a solvent such as ethyl acetate, tetrahydrofuran or the like, at a temperature in the range of from about 25° C. to about 70° C. A mineral acid catalyst such as sulfuric acid is used in addition to the palladium catalyst.

The conversion of a compound of formula XV to a compound of formula Ic can be carried out by treatment with boron tribromide in a solvent such as methylene chloride, 1,2-dichloroethane or the like, at a temperature in the range of from about −70° C. to about 25° C.

It is understood that preferably any intermediate prepared in Reaction Schemes I–V is recovered and isolated utilizing known procedures, for example, by precipitation, crystallization, chromatography or the like, prior to use in the next reaction step. The end products of formula I are recovered by similar known procedures.

The invention also relates to salts of the compound of formula I, when $R_1$ is hydrogen, which are prepared by the reaction of the acids with a base having a non-toxic, pharmacologically acceptable cation. In general, any base which will form a salt with a carboxylic acid and whose pharmacological properties will not cause an adverse physiological effect is within the scope of this invention. Suitable bases thus include, for example, the alkali metal and alkaline earth metal hydroxides, carbonates, and the like, for example, calcium hydroxide, sodium hydroxide, sodium carbonate, potassium carbonate and the like, ammonia, primary, secondary and tertiary amines, such as monoalkylamines, dialkylamines, trialkylamines, for example, methylamine, diethylamine, triethylamine and the like, and nitrogen containing heterocyclic amines, for example, piperidine and the like. A salt thus produced is the functional equivalent of the corresponding compound of formula I wherein $R_1$ is hydrogen, and one skilled in the art will appreciate that the variety of salts embraced by the invention is limited only by the criterion that a base employed in forming the corresponding salts be both non-toxic and Physiologically acceptable.

The compounds of formula I exhibit activity, for example, $\Delta^5$-lipoxygenase inhibitors, and as hereinafter further described. The useful pharmacological activities of the compounds of formula I can be demonstrated by the tests hereinafter set forth.

The compounds of formula I are useful as agents for the treatment of inflammatory diseases such as inflammatory bowel disease. Inflammatory bowel disease (IBD) includes a variety of diseases of the gastrointestinal (GI) tract such as Crohn's disease of the colon and ileum, ulcerative colitis and pseudomembranous colitis. Common symptoms of these diseases include inflammation of the affected area of the GI mucosa, mucosa ulceration, edema, infiltration of the mucosa with inflammatory cells and severe diarrhea. Arachidonic acid metabolites from the $\Delta^5$-LO pathway are believed to mediate IBD.

IN VITRO TEST FOR $\Delta^5$-LIPOXYGENASE INHIBITORS

Compounds of formula I of the invention were tested for their effect on $\Delta^5$-lipoxygenase from rat basophilic leukemia (RBL-1) cells. The activity of this enzyme was determined by measuring the catalytic conversion of [1-$^{14}$C]arachidonic acid to [1-$^{14}$C-5-hydroperoxy-6,8,11,14-eicosatetraenoic acid ([1-$^{14}$C]-5-HPETE) which leads to the formation of the 5-hydroxy derivative ([1-$^{14}$C]-5-HETE). The $\Delta^5$-lipoxygenase was derived from the supernatant fraction of lysed RBL-1 cells using a modification of the method previously described by Jakschik and Lee [Nature 287:51 (1980)]. Briefly, RBL-1 cells were lysed by homogenization in ice-cold buffer (50 mM Tris-HCl buffer, pH 7.2, containing 1 mM EDTA and 14 µM indomethacin). The homogenate was centrifuged at 4° C. and 49,000 g for 20 minutes and the resulting supernatant fraction was used as the source of $\Delta^5$-lipoxygenase. The enzyme was assayed at 37° C. using 6.7 µM (0.39 µCi/ml) [1-$^{14}$C]arachidonic acid as the substrate in 50 mM Tris-HCl buffer, pH 7.2, containing 1 mM glutathione, 2 mM $CaCl_2$, 14 µM indomethacin, and 0.25 to 0.50 mM EDTA. The mixture was incubated for 10 minutes and the reaction was stopped by the addition of citric acid and diethyl ether. The ethereal extract containing [1-$^{14}$C]-5-HETE and unreacted substrate analyzed by silica gel TLC using isooctane-methylethyl ketone acetic acid (100:9:1) as the developing solvent. The major radioactive spots were located using a Berthold TLC scanner. The [1-$^{14}$C]-5-HETE was identified by co-chromatography with an authentic, chemically synthesized [1-$^{14}$C]-5-HETE standard. The $R_f$ values for [1-$^{14}$C]-5-HETE, unconverted [1-$^{14}$C]arachidonic acid, and unidentified radioactive polar products were 0.49, 0.95, and 0.04, respectively. The effect of inhibitors on $\Delta^5$-lipoxygenase activity was determined by preincubating the enzyme for 10 minutes at 30° C. in the presence or absence of various concentrations of the drug prior to addition of substrate. This test has been described by W. C. Hope, A. F. Welton, C. Fiedler-Nagy, C. Batuta-Bernardo and J. F. Coffey in Biochemical Pharmacology 32:362 (1983).

In this test 4-[[6-(6,7-dihydroxy-2-naphthalenyl)-6-oxohexyl]oxy]-2-hydroxy-3-propylbenzoic acid exhibits an dihydroxy-2-naphthalenyl)butoxy]-2-hydroxy-3-propylbenzoic acid exhibits an $IC_{50}$ of 4.7 nM.

RAT PERITONEAL MACROPHAGE ASSAY, IN VITRO

The rat peritoneal macrophage assay measures the ability of a test compound to influence the release of arachidonic acid (AA) from phospholipid stores in the plasma membrane and the subsequent metabolism of AA by the $\Delta^5$-lipoxygenase (5-LO) and cyclooxygenase (CO) pathways to the final products excreted by the cells: leukotriene $B_4$ (LTB4, from the 5-LO pathway) and prostaglandin $E_2$(PGE2, from the CO Pathway).

Macrophages were obtained from rats by peritoneal lavage with phosphate buffered saline minus $Ca^{+2}$ and $Mg^{+2}$ (PBS). Cells were washed 3 times with PBS and resuspended in Delbecco's Modified Eagle medium (Gibco Laboratories) containing L-glutamine and D-glucose and supplemented with 10% fetal calf serum. Cells were counted on a Coulter ZBA cell counter and then resuspended to a concentration of $4 \times 10^6$ cells/mL. Three mL of the cell suspension were added to plastic culture dishes (3 cm), and then the cells were allowed to adhere for 90 minutes at 37° C. Dishes were washed 3 times with PBS to remove nonadherent cells. $^{14}$C-AA (ca. 54 µCi/mmol) was added to the cells (1 µCi/dish) and allowed to incorporate for 90 minutes. Unincorporated $^{14}$C-AA was removed and the cell layer was again washed 3 times with PBS. Test compounds were dissolved in DMSO and diluted in phosphate-buffered Hank's balanced salt solution to appropriate concentrations. Cells were incubated with test compounds or the solvent used to dissolve the test compounds (control) for 30 minutes at 37° C. and were then stimulated with calcium ionophore A 23187 ($5 \times 10^{-7}$M) for 20 minutes. The extracellular fluid was removed and $^{14}$C radioactivity released into this fluid from AA metabolism was measured by liquid scintillation spectroscopy. The amounts of LTB4 and PGE2 were measured in the extracellular fluid by radioimmunoassay with specific antisera. The effect of a test compound or standard was calculated as a Percent inhibition of the maximum effect produced in the presence of A 23187 and expressed as an inhibitory concentration 50% ($IC_{50}$).

This assay measures inhibition by the test compounds of the 5-LO and the CO pathways of AA metabolism and this inhibition is expressed as an $IC_{50}$ for LTB4 and PGE2 formation, respectively.

In this test 4-[[6-(6,7-dihydroxy-2-naphthalenyl)-6-oxohexyl]oxy]-2-hydroxy-3-propylbenzoic acid exhibits $IC_{50}$ values of 3µM for LTB4 and 2µM for PGE2 formation and 4-[4-(6,7-dihydroxy-2-naphthalenyl)butoxy]-2-hydroxy-3 propylbenzoic acid exhibits $IC_{50}$ values of 3µM for LTB4 and 2µM for PGE2 formation.

Acetic Acid-Induced Colitis in Rats, In Vivo

The rat acetic acid-induced colitis bioassay has been described by J. E. Krawisz, et al. in Amer. J. Proc. Gastro. Col. Rec. Surg. 31: 11–18 (1980), and by P. Sharon and W. F. Stenson in Gastroenterolgy 88: 55–63 (1985) and 86:453–460 (1984). Acetic acid-induced colitis is characterized by the movement of inflammatory cells into the colon, with the number of such cells in the mucosa being measured by the activity of myeloperoxidase, a marker enzyme for these cells. Positive desirable activity is indicated by a reduction in the high levels of myeloperoxidase caused by acetic acid. Male rats (Sprague-Dawley), weighing 150 to 300 g, were pretreated twice daily for two days with either the vehicle (water, or dimethylsulfoxide) or the test inhibitor compound suspended in water or dissolved in dimethylsulfoxide and orally administered. On the third day, the animals were dosed the same as on the previous two days, anesthetized with metofane, and 2 ml of 2.5% acetic acid was injected by syringe into the colonic lumen, followed immediately by 3 ml of air and a rinse consisting of 3 ml of phosphate-buffered saline (the acetic acid is Present in the lumen for a sufficient period to cause inflammation without producing severe necrosis or irreversible damage). The animals were administered a second dose of the test compound in the same amount about 16 hours later. Twenty four hours after the acetic acid treatment, the animals were sacrificed, the colonic mucosa was surgically removed and homogenized in an aqueous buffer at pH 6 with a Tissumizer or similar device, and myeloperoxidase was measured in the homogenate using o-phenylenediamine as a chromagen, as described by A. Voller, D. E. Bidwell and A. Bartlett in The Enzyme Linked Immunosorbent Assay (ELISA), Zoological Soc., London, 1979, pages 29–30. Control animals were pretreated with the vehicle and saline in place of acetic acid.

Data for representative compounds of this invention are reported in Table I.

TABLE I

| Compound | Rat Acetic Acid Colitis Model | |
|---|---|---|
| | Dose mg/kg p.o. | % Inhibition of Myeloperoxidase Accumulation |
| 4-[6-(6,7-Dihydroxy-2-naphthalenyl)hexyloxy]-2-hydroxy-3-propylbenzoic acid | 1 | 46 ± 12 |
| 4-[5-(6,7-Dihydroxy-2-naphthalenyl)pentyloxy]-2-hydroxy-3-propylbenzoic acid | 10 | 56 ± 11 |
| 4-[4-(6,7-Dihydroxy-2-naphthalenyl)butoxy]-2-hydroxy-3-propylbenzoic acid | 3 | 82 ± 8 |
| 4-[3-(6,7-Dihydroxy-2-naphthalenyl)propoxy]-2-hydroxy-3-propylbenzoic acid | 1 | 21 ± 4 |
| 4-[2-(6,7-Dihydroxy-2-naphthalenyl)ethoxy]-2-hydroxy-3-propylbenzoic acid | 10 | 60 ± 13 |
| 4-[6-(6,7-Dihydroxy-2-naphthalenyl)hexyloxy]benzoic acid | 10 | 68 ± 13 |
| 4-[6-(6,7-Dihydroxy-2-naphthalenyl)hexyloxy]-2-hydroxybenzoic acid | 1 | 65 ± 9 |
| 4-[[6-(6,7-Dihydroxy-2-naphthalenyl)-6-oxohexyl]oxy]-2-hydroxy-3-propylbenzoic acid | 1 | 83 ± 19 |
| 4-[[5-(6,7-Dihydroxy-2-naphthalenyl)-5-oxopentyl]oxy]-2-hydroxy-propylbenzoic acid | 30 | 80 ± 18 |
| 4-[[6-(6,7-Dihydroxy-2-naphthalenyl)-6-oxohexyl]oxy-2-hydroxy-3-propylbenzoic acid | 1 | 43 ± 11 |
| 4-[4-(5,8-Dichloro-6,7-dihydroxy-2-naphthalenyl)butoxy]-2-hydroxy-3-propylbenzoic acid | 10 | 71 ± 7 |

TABLE I-continued

| Compound | Rat Acetic Acid Colitis Model | |
|---|---|---|
| | Dose mg/kg p.o. | % Inhibition of Myeloperoxidase Accumulation |
| zoic acid | | |

A compound of formula I or a salt thereof or a composition containing a therapeutically effective amount of a compound of formula I or salt can be administered by methods well known in the art. Thus, a compound of formula I or a salt thereof can be administered either singly or with other pharmaceutical agents, orally or rectally. For oral administration the described compound can be administered in the form of tablets, capsules, for example, in admixture with talc, starch, milk sugar or other inert ingredients, that is, pharmaceutically acceptable carriers, in the form of aqueous solutions, suspensions, elixirs or aqueous alcoholic solutions, for example, in admixture with sugar or other sweetening agents, flavoring agents, colorants, thickeners and other conventional Pharmaceutical excipients, or beadlets for oral administration. For rectal administration, the desired compound can be administered in the form of suppositories utilizing an inert carrier material, such as cocoa butter or the like.

In the practice of the invention, the dose of a compound of formula I or a salt thereof to be administered and the frequency of administration will be dependent on the potency and duration of activity of the particular compound or salt and on the route of administration, as well as the severity of the condition, age of the mammal to be treated and the like. Oral doses of a compound of formula I or salt contemplated for use in practicing the invention are in the range of from about 25 to about 1000 mg per day, preferably from about 25 to about 250 mg, either as a single dose or in divided doses.

The Examples which follow further illustrate the invention. All temperatures set forth in the Examples are in degrees Centigrade. Melting points were taken on a Thomas Hoover capillary melting point apparatus and are uncorrected. All compounds were characterized by proton magnetic resonance spectra taken on a Varian XL-100 or SL-200 spectrometer and mass spectra taken on a CEC 21-110 mass spectrometer at 70 eV. Preparative high-performance liquid chromatography (HPLC) was performed on silica gel Prep-Pak 500 cartridges using a Waters Associates Prep LC 500A. Extracts were dried over anhydrous magnesium sulfate unless otherwise noted.

EXAMPLE 1

2-Hydroxy-4-(2-propenyloxy)benzoic acid methyl ester

A mixture of 102 g (0.607 mol) of methyl 2,4-dihydroxybenzoate, 54 mL (0.619 mol) of allyl bromide and 126 g (0.91 mol) of anhydrous potassium carbonate in 300 mL of anhydrous acetone was stirred at reflux for 3 hours. The reaction mixture was filtered and the solid was washed with acetone. After removal of the acetone from the filtrate under reduced Pressure, the residue was distilled to give 85 g (67% yield), boiling point 106°–108° C. /0.3 mm of 2-hydroxy-4(2-propenyloxy)-benzoic acid methyl ester.

EXAMPLE 2

2,4-Dihydroxy-3-(2-propenyl)benzoic acid methyl ester 81 g of 2-hydroxy-4-(2-propenyloxy)benzoic acid methyl ester was heated in an oil bath under argon until the internal temperature reached 180°–185° C. The temperature was maintained in this range for 1½ hours and then raised to 210° C. for 1½ hours. After cooling, the oil crystallized and was recrystallized from ether-petroleum ether to give 37 g (46% yield), mp 65°–66° C. of 2,4-dihydroxy-3-(2-propenyl)benzoic acid methyl ester. Anal Calcd for $C_{11}H_{12}O_4$: C, 63.46; H, 5.81; Found: C, 63.65; H, 6.09.

EXAMPLE 3

2,4-Dihydroxy-3-propylbenzoic acid methyl ester

A solution of 54 g of 2,4-dihydroxy-3-(2-propenyl)-benzoic acid methyl ester in 900 mL of ethanol and 3g of 10% palladium on carbon was shaken in a hydrogen atmosphere until the uptake ceased (45 minutes). The catalyst was removed by filtration through Celite and the filtrate was concentrated under reduced pressure to an oil which solidified. After stirring with hexane, the product was filtered to give 51 g, mp 66°–68°, of 2,4-dihydroxy-3-propylbenzoic acid methyl ester.

Anal. Calcd for $C_{11}H_{14}O_4$: C, 62.85; H, 6.71. Found: C, 62.95; H. 6.74.

EXAMPLE 4

2,4-Dihydroxy-3-propylbenzoic acid phenylmethyl ester

A solution of 37 g (0.18 mol) of 2,4-dihydroxyl-3-propylbenzoic acid methyl ester in 750 mL of methanol and 415 mL of 3N sodium hydroxide was stirred at reflux for 3 hours. The methanol was removed under reduced pressure and the residue was treated with water and 6N hydrochloric acid to acidify. The solid product was extracted with ethyl acetate and the extract was dried and concentrated under reduced pressure to a tan solid, which was used without purification. This crude acid (35 g, 0.18 mol), 23 mL (0.2 mol) of benzyl chloride and 17 g (0.2 mol) of sodium bicarbonate in 250 mL of anhydrous dimethylformamide was stirred and heated at 60° C. for 23 hours. The solvent was removed under reduced pressure, the residue was treated with saturated sodium bicarbonate solution, and the product was extracted with ethyl acetate. The dried extract was concentrated under reduced pressure and the residual oil was purified by HPLC using 15% ethyl acetate-hexane, to give 36 g (70% yield), mp 86°–88° C. of 2-4,dihydroxy-3-propylbenzoic acid phenylmethyl ester.

EXAMPLE 5

5 6-Bromo-1-(6,7-dimethoxy-2-naphthalenyl)-1-hexanone

Aluminum chloride (2.7 g, 0.02 mole) was added to a solution of 5.0 g (0.02 mole) of 6-bromohexanoyl chloride in 40 mL of anhydrous methylene chloride. To the resulting solution, cooled in an ice bath, was added 3.3 g (0.017 mole) of 2,3-dimethoxynaphthalene. After stirring for one hour in the ice bath, the reaction mixture was left at room temperature for 17 hours. Water was added, the organic layer was separated and washed with sodium bicarbonate solution. The extract was dried and concentrated under reduced pressure. Crystallization from ethyl acetate-hexane gave 3.8 g (59% yield), mp 81°–82° C., of 6-bromo-1-(6,7-dimethoxy-2-naphthalenyl)-1-hexanone.

Anal. Calcd. for $C_{18}H_{21}BrO_3$: C, 59.19; H, 5.80; Br, 21.88. Found: C, 59.06; H, 5.78; Br, 21.82.

EXAMPLE 6

2-(6-Bromohexyl)-6,7-dimethoxynaphthalene

A mixture of 16.3 g (0.045 mole) of 6-bromo-1-(6,7-dimethoxy-2-naphthalenyl)-1-hexanone and 2 g of 10% palladium on carbon in 200 mL of acetic acid and 4 drops of concentrated sulfuric acid was shaken under 50 Psi of hydrogen pressure in a Parr hydrogenator for 22 hours. The reaction mixture was filtered through Celite and the filtrate was concentrated under reduced pressure to a solid. Recrystallization from ether-hexane gave 9.9 g (63% yield), mp 74°–76°, of 2-(6-bromohexyl)-6,7-dimethoxynaphthalene.

Anal Calcd. for $C_{18}H_{23}BrO_2$: C, 61.54; H, 6.60; Br, 22.75. Found: C, 61.69; H, 6.67; Br, 22.91.

EXAMPLE 7

2-(6-Bromohexyl)-6,7-bis(phenylmethoxy)naphthalene

To 9.88 g (0.028 mole) of 2-(6-bromohexyl)-6,7-dimethoxynaphthalene in 200 mL of anhydrous methylene chloride, cooled at −70° C. under an argon atmosphere, was added 71 mL (0.071 mole) of 1M boron tribromide in methylene chloride dropwise over 30 minutes. The reaction mixture was stirred at −70° C. for 30 minutes and then kept at −20° C. for 22 hours. Water (100 mL) was added and the organic layer was separated and concentrated under reduced pressure. The residue was dissolved in 400 mL of ether and the solution was shaken with 100 mL of 1N hydrochloric acid for 5 minutes. The ether layer was washed with sodium bicarbonate solution, dried and concentrated under reduced pressure to yield a tan solid (9.12 g). A mixture of 8.62 g (0.027 mole) of this solid, 9.5 mL (0.08 mole) of benzyl bromide and 11 g (0.08 mole) of potassium carbonate in 150 mL of acetone was stirred at reflux for 48 hours. The reaction mixture was concentrated under reduced pressure and the residue was treated with 100 mL of ethyl acetate-hexane (1:1). Salts were removed by filtration and the product was purified by HPLC using 5% ethyl acetate-hexane, to give 8.6 g (64% yield), mp 64°–66°, of 2-(6-bromohexyl)-6,7-bis(phenylmethoxy)naphthalene after recrystallization from ether-hexane.

Anal. Calcd. for $C_{30}H_{31}BrO_2$ C, 71.57; H, 6.21; Br, 15.87. Found: C, 71.58; H, 6.17; Br, 15.98.

EXAMPLE 8

5-Bromo-1-(6,7-dimethoxy-2-naphthalenyl)-1-pentanone

Aluminum chloride (18.4 g, 0.138 mole) was added to a solution of 27.7 g (0.138 mole) of 5-bromopentanoyl chloride in 150 mL of methylene chloride. To the resulting solution cooled in an ice bath was added dropwise a solution of 21.6 g (0.115 mole) of 2,3-dimethoxynaphthalene in 100 mL of methylene chloride over 30 minutes. The reaction mixture was stirred at 3° C. for 4 hours and at 24° C. for 5 hours. The reaction mixture was worked up as in Example 5 and the crude product was recrystallized from acetone-hexane, to give 26.5 g (66% yield), mp 93°–95°, of 5-bromo-1-(6,7-dimethoxy-2-naphthalenyl)-1-pentanone.

Anal. Calcd. for $C_{17}H_{19}BrO_3$: C, 58.13; H, 5.45; Br, 22.75. Found: C, 57.70; H, 5.41; Br, 22.69.

EXAMPLE 9
2-(4-Chlorobutyl)-6,7-dimethoxynaphthalene

Aluminum chloride (25.5 g, 0.19 mole) was added to a solution of 21.5 mL (0.19 mole) of 4-chlorobutyryl chloride in 225 mL of methylene chloride. To the resulting solution, cooled in an ice bath, was added dropwise a solution of 30.0 g (0.16 mole) of 2,3-dimethoxynaphthalene in 150 mL of methylene chloride over 30 minutes. The reaction mixture was stirred at 3° C. for 30 minutes and at 24° C. for 17 hours. The reaction mixture was worked up as Example 5 and the crude product was recrystallized from acetone-hexane, to give 31.5 g (68% yield), mp 98°–99°, of 4-chloro-1-(6,7-dimethoxy-2-naphthalenyl)-1-butanone.

Anal Calcd. for $C_{16}H_{17}ClO_3$: C, 65.64; H, 5.85; Cl, 12.11. Found: C, 65.33; H, 5.77; Cl, 12.16.

A mixture of 31.5 g of 4-chloro-1-(6,7-dimethoxy-2-naphthalenyl)-1-butanone and 3 g of 10% palladium on carbon in 300 mL of acetic acid and 5 drops of concentrated sulfuric acid was shaken under 50 psi of hydrogen pressure in a Parr hydrogenator for 9 hours. The reaction was worked up as in Example 6 and the crude Product was recrystallized from ether-hexane, to give 19.6 g (65% yield), mp 67°–69°, of 2-(4-chlorobutyl)-6,7-dimethoxynaphthalene.

Anal. Calcd. for $C_{16}H_{19}ClO_2$: C, 68.94; H, 6.87; Cl, 12.72. Found: C, 68.75; H, 6.92; Cl, 12.89.

EXAMPLE 10
2-(4-Chlorobutyl)-6,7-bis(phenylmethoxy)naphthalene

To 17.0 g (0.061 mole) of 2-(4-chlorobutyl)-6,7-dimethoxynaphthalene in 350 mL of methylene chloride cooled at −70° C. under an argon atmosphere was added 122 mL (0.122 mole) of 1M boron tribromide in methylene chloride, dropwise over 30 minutes. The reaction mixture was stirred for 30 minutes at −70° C. and then kept at −20° C. for 17 hours. Workup as in Example 7 gave 2-(4-chlorobutyl)-6,7-dihydroxynaphthalene as a colorless solid (15.3g). This solid, 21.8g (0.18 mole) of benzyl bromide and 25.3g (0.18 mole) of potassium carbonate in 300 mL of acetone was stirred at reflux for 18 hours. Workup as in Example 7 and purification of the crude product by HPLC using 5% ethyl acetate-hexane gave a solid which was recrystallized from ether-hexane, to give 13.0 g (49% yield), mp 54°–59°, of 2-(4-chlorobutyl)-6,7-bis(phenylmethoxy)naphthalene.

Anal Calcd. for $C_{28}H_{27}ClO_2$: C, 78.03; H, 6.31; Cl, 8.23. Found: C, 78.08; H, 6.24; Cl, 8.14.

EXAMPLE 11
2-(3-Chloropropyl)-6,7-dimethoxynaphthalene

Aluminum chloride (4.2g, 0.031 mole) was added to a solution of 3.0 mL (0.031 mole) of 3-chloropropionyl chloride in 50 mL of methylene chloride. To the resulting solution cooled in an ice bath was added dropwise a solution of 4.95 g (0.026 mole) of 2,3-dimethoxynaphthalene in 30 mL of methylene chloride. The reaction mixture was stirred at 3° C. for 45 minutes and at 24° C. for 16 hours. Workup as in Example 5 and recrystallization of the crude product from ethyl acetate-hexane gave 4.70 g (65% yield), mp 136°–137°, of 3-chloro-1-(6,7-dimethoxy-2-naphthalenyl)-1-propanone.

Anal. Calcd. for $C_{15}H_{15}ClO_3$: C, 64.64; H, 5.42; Cl, 12.72. Found: C, 63.83; H, 5.08; Cl, 12.62.

A mixture of 4.7 g of 3-chloro-1-(6.7-dimethoxy-2-naphthalenyl)-1-propanone and 1.0 g of 10% palladium on carbon in 100 mL of acetic acid, 50 mL of ethyl acetate and 2 drops of concentrated sulfuric acid was shaken under 54 psi of hydrogen pressure in a Parr hydrogenator for 5 hours. Workup as in Example 6 and chromatography of the crude product on 200 g of silica gel using 30% ethyl acetate-hexane gave 2.88 g (65% yield), mp 49°–53°, of 2-(3-chloropropyl)-6,7-dimethoxynaphthalene.

Anal. Calcd. for $C_{15}H_{17}ClO_2$: C, 68.05; H, 6.47; Cl, 13.39. Found: C, 67.89; H, 6.39; Cl, 13.20.

EXAMPLE 12
1,4-Dichloro-6-(4-chlorobutyl)-2,3-dimethoxynaphthalene

To a stirred solution of 3.0 g (0.011 mole) of 2-(4-chloro-butyl)-6,7-dimethoxynaphthalene in 25 mL of methylene chloride cooled in an ice bath was added 1.8 mL (0.023 mole) of sulfuryl chloride in 10 mL of methylene chloride over 15 minutes. The reaction mixture was stirred at 3° C. for 30 minutes, at 24° C. for 6 hours and then was washed with sodium bicarbonate solution, dried and concentrated under reduced pressure. Purification by HPLC using 2.5% ethyl acetate-hexane gave 3.32 g (79% yield) of 1,4-dichloro-6-(4-Chlorobutyl)-2,3-dimethoxynaphthalene as an oil.

Anal. Calcd. for $C_{16}H_{17}Cl_3O_2$: C, 55.28; H, 4.93; Cl, 30.59. Found: C, 55.24; H, 4.84; Cl, 30.78.

EXAMPLE 13
2-Hydroxy-4-[[6-(6,7-dimethoxy-2-naphthalenyl)-6-oxohexyl]-oxy]-3-propylbenzoic acid methyl ester A mixture of 3.80 g (0.0104 mole) of 6-bromo-1-(6,7-dimethoxy-2-naphthalenyl)-1-hexanone, 2.18 g (0.0104 mole) of 2,4-dihydroxy-3-propylbenzoic acid methyl ester, 2.9 g (0.02 mole) of potassium carbonate and 0.3 mL (0.93 mmole) of tris-[2-(2-methoxyethoxy)ethyl]amine (TDA-1) in 80 mL of toluene was stirred at reflux for 46 hours. The reaction mixture was filtered and the filtrate was concentrated under reduced pressure to a solid. Recrystallization from ethyl acetate-hexane gave 4.2 g (82% yield), mp 111°–112°, of 2-hydroxy-4[[6-(6,7-dimethoxy-2-naphthalenyl)-6-oxohexyl]oxy]-3-propylbenzoic acid methyl ester.

Anal. Calcd. for $C_{29}H_{34}O_7$: C, 70.43; H, 6.93. Found: C, 70.28; H, 6.98.

EXAMPLE 14
2-Hydroxy-4-[[6-(6,7-dimethoxy-2-naphthalenyl)-6-oxohexyl]oxy]3-propylbenzoic acid A solution of 4.2 g (0.0085 mole) of 2-hydroxy-4-[[6-(6,7-dimethoxy-2-naphthalenyl)-6-oxohexyl]oxy]-3-propylbenzoic acid methyl ester in 100 mL of methanol, 50 mL of dioxane and 34 mL (0.034 mole) of 1N sodium hydroxide was stirred at reflux for 8 hours. The reaction mixture was concentrated under reduced pressure, the residue was acidified and the product was extracted with ethyl acetate. The dried extract was concentrated and the crude product was recrystallized from a methanol and water mixture to give 3.48 g, mp 144°–146°, of 2-hydroxy-4-[[6-(6,7-dimethoxy-2-naphthalenyl)-6-oxohexyl]oxy-3-propylbenzoic acid.

Anal. Calcd. $C_{28}H_{32}O_7$: C, 69.98; H, 6.71. Found: C, 69.58; H, 6.77.

EXAMPLE 15

4-[[6-(6,7-Dihydroxy-2-naphthalenyl)-6-oxohexyl]-oxy1-2-hydroxy3-propylbenzoic acid To a solution of 2.0 g (0.0042 mole) of 2-hydroxy-4-[[6-(6,7-dimethoxy-2-naphthalenyl)-6-oxohexyl]oxy]-3-propylbenzoic acid in 120 mL of methylene chloride, cooled at −70° C. under argon, was added 15 mL (0.015 mole) of 1M boron tribromide in methylene chloride. After 5 minutes, the reaction mixture was removed from the cooling bath and kept at −20° C. for 7 hours. Water (50 mL) was added and the organic layer was concentrated under reduced pressure. The residue was dissolved in ether (200 mL) and the solution was shaken vigorously with 100 mL of 3N hydrochloric acid for 5 minutes. The ether layer was dried, concentrated under reduced pressure and the residue was recrystallized from ethyl acetate-hexane, to give 1.46 g (78% yield), mp 205°–207°, of 4-[[6-(6,7-dihydroxy-2-naphthalenyl)-6-oxohexyl]oxy]-2-hydroxy-3-propylbenzoic acid.

Anal. Calcd. for $C_{26}H_{28}O_7$: C, 69.01; H, 6.24. Found: C, 68.71; H, 6.43.

EXAMPLE 16

2-Hydroxy-4-[[6-(6,7-dimethoxy-2-naphthalenyl)-6-oxohexyl]oxy]-3-propylbenzoic acid phenylmethyl ester A mixture of 7.60 g (0.021 mole) of 6-bromo-(6,7-dimethoxy-2-naphthalenyl)-1-hexanone, 5.96 g (0.021 mole) of 2,4-dihydroxy-3-propylbenzoic acid phenylmethyl ester, 5.75 g (0.042 mole) of potassium carbonate and 3.20 g (0.021 mole) of sodium iodide in 100 mL of acetone and 25 mL of dimethylformamide was stirred at reflux for 26 hours. The solvents were removed under reduced pressure and the crude product was purified by HPLC using 2% ethyl acetate-toluene, to give 8.14 g (69% yield) of 2-hydroxy-4-[[6,7-dimethoxy-2-naphthalenyl)-6-oxohexyl]oxy]-3-propylbenzoic acid phenylmethyl ester.

Anal. Calcd. for $C_{35}H_{38}O_7$: C, 73.66; H, 6.71. Found: C, 73.44; H, 6.56.

EXAMPLE 17

2-Hydroxy-4-[[6-(6,7-dimethoxy-2-naphthalenyl)-6-oxohexyl]oxy]-3-propylbenzoic acid A mixture of 8.1 g of 2-hydroxy-4-[[6-(6,7-dimethoxy-2-naphthalenyl)-6-oxohexyl]oxy]-3-propylbenzoic acid phenylmethyl ester and 0.6 g of 10% palladium on carbon in 300 mL of tetrahydrofuran was shaken in a hydrogen atmosphere for 3 hours. The reaction mixture was filtered through Celite and the filtrate was concentrated under reduced pressure to a solid Recrystallization from acetone-water gave 5.0 g (73% yield), mp 167°–168°, of 2-hydroxy-4-[[6-(6,7-dimethoxy-2-naphthalenyl)-6-oxohexyl]oxy]-3-propylbenzoic acid.

EXAMPLE 18

4-[[6-(6,7-Dihydroxy-2-naphthalenyl)-6-oxohexyl]oxy]-2-hydroxy-3-propylbenzoic acid ethyl ester A mixture of 1.0 g (2.2 mmole) of 4-[[6-(6,7-dihydroxy-2-naphthalenyl)-6-oxohexyl]oxy]-2-hydroxy-3-propylbenzoic acid, 1.8 mL (22 mmole) of ethyl iodide and 0.20 g (2.4 mmole) of sodium bicarbonate in 15 mL of dimethylformamide was stirred and heated at 50° C. for 7 hours. The solvent was removed under reduced pressure and the product was extracted with ethyl acetate. The dried extract was concentrated and the product was recrystallized from acetone-hexane to give 0.82 g (77% yield), mp 170°–172°, of 4-[[6-(6,7-dihydroxy-2-naphthalenyl)-6-oxohexyl]oxy]-2-hydroxy-3-propylbenzoic acid ethyl ester.

Anal Calcd for $C_{28}H_{32}O_7$: C, 69.98; H, 6.71. Found: C, 69.90; H, 6.87.

EXAMPLE 19

2-Hydroxy-4-[6-(6,7-dimethoxy-2-naphthalenyl)hexyloxy]-3-propylbenzoic acid

A mixture of 1.5 g of 2-hydroxy-4-[[6-(6,7-dimethoxy-2-naphthalenyl)-6-oxohexyl]oxy]-3-propylbenzoic acid and 0.4 g of 10% palladium on carbon in 40 mL of acetic acid, 40 mL of ethyl acetate and 1 drop of concentrated sulfuric acid was shaken under 53 psi of hydrogen pressure in a Parr hydrogenator for 5 ½ hours. Workup as in Example 6 and recrystallization of the crude product from ethyl acetate-hexane gave 1.06 g, mp 102°–104°, of 2-hydroxy-4-[6-(6,7-dimethoxy-2-naphthalenyl)hexyloxy]-3-propylbenzoic acid.

Anal. Calcd. for $C_{28}H_{34}O_6$: C, 72.08; H, 7.35. Found: C, 71.94; H, 7.36.

EXAMPLE 20

4-[6-(6.7-Dihydroxy-2-naphthalenyl)hexyloxy]-2-hydroxy-3-propylbenzoic acid

To a solution of 1.05 g (2.25 mmole) of 2-hydroxy-4-[6-(6,7-dimethoxy-2-naphthalenyl)hexyloxy]-3-propylbenzoic acid in 60 mL of methylene chloride cooled at −70° C. under argon was added 8 mL (8 mmole) of 1M boron tribromide in methylene chloride. The reaction mixture was kept at −20° C. for 16 hours. Workup as in Example 15 and recrystallization of the crude product from ether-methylene chloride gave 0.72 g, mp 154°–158°, of 4-[6-(6,7-dihydroxy-2-naphthalenyl)hexyloxy]-2-hydroxy-3-propylbenzoic acid.

Anal. Calcd. for $C_{26}H_{30}O_6$: C, 71.21; H, 6.90. Found: C, 71.31; H, 6.84.

EXAMPLE 21

2-Hydroxy-4-[6-[6,7-bis(phenylmethoxy)-2-naphthalenyl]hexyloxy]-3-propylbenzoic acid phenylmethyl ester A mixture of 2.38 g (4.73 mmole) of 2-(6-bromohexyl)-6,7bis(phenylmethoxy)naphthalene, 1.35 g (4.73 mmole) of 2,4-dihydroxy-3-propylbenzoic acid phenylmethyl ester, 1.3 g (9.45 mmole) potassium carbonate, 0.7 g (4.73 mmole) sodium iodide in 40 mL of acetone-5 mL of dimethylformamide was stirred at reflux for 48 hours. Workup as in Example 16 and recrystallization of the crude product from methylene chloride-methanol gave 2.64 g (79% yield), mp 94°–97° C., of 2-hydroxy-4-[6-[6,7-bis(phenylmethoxy)-2-naphthalenyl]hexyloxy]3-propylbenzoic acid phenylmethyl ester. C, 79.33; H, 6.64.

EXAMPLE 22

4-[6-(6,7-Dihydroxy-2-naphthalenyl)hexyloxy]-2-hydroxy-3propylbenzoic acid

A mixture of 2.6 g of 2-hydroxy-4-[6-[6,7-bis(phenylmethoxy)-2-naphthalenyl]hexyloxy]-3-propylbenzoic acid phenylmethyl ester and 0.4 g of 10% palladium on carbon in 200 mL of tetrahydrofuran was shaken in a hydrogen atmosphere for 10 hours. Workup as in Example 17 and recrystallization from ether-methylene chloride gave 1.17 g (73% yield), mp 165°–167° C., of 4-[6-(6,7-dihydroxy-2-naphthalenyl)hexyloxy]-2-hydroxy-3-propylbenzoic acid.

EXAMPLE 23

2-Hydroxy-4-[4-(6,7-dimethoxy-2-naphthalenyl)butoxy]-3propylbenzoic acid methyl ester A mixture of 3.16 g (11.3 mmole) of 2-(4-chlorobutyl)-6,7dimethoxynaphthalene, 2.34 g (11.2 mmole) of 2,4-dihydroxy3-propylbenzoic acid methyl ester, 3.1 g (22.5 mmole) of potassium carbonate and 2.0 g (13.3 mmole) of sodium iodide in 50 mL of acetone-25 mL of dimethylformamide was stirred at reflux for 18 hours. Workup as in Example 16 and purification of the crude product by HPLC using 15% ethyl acetate-hexane gave 4.08 g (80% yield) of 2-hydroxy-4-[4-(6/7-dimethoxy-2-naphthalenyl)butoxy]-3-propylbenzoic acid methyl ester as an oil.

Anal Calcd. for $C_{27}H_{32}O_6$: C, 71.66; H, 7.13. Found C, 70.96; H, 7.31.

EXAMPLE 24

2-Hydroxy-4-[4-(6,7-dimethoxy-2-naphthalenyl)butoxy]-3-propylbenzoic acid

A solution of 4.05 g (8.8 mmole) of 2-hydroxy-4-[4-(6,7-dimethoxy-2-naphthalenyl)butoxy-3-propylbenzoic acid methyl ester in 100 mL of methanol-50 mL of dioxane and 35 mL of 1N sodium hydroxide was stirred at reflux for 16 hours. Workup as in Example 14 and recrystallization from ethyl acetate-hexane gave 3.34 g (87% yield), mp 147°–148° C., of 2-hydroxy-4-[4-(6,7-dimethoxy-2-naphthalenyl)butoxy]-3-propylbenzoic acid.

Anal. Calcd. for $C_{26}H_{30}O_6$: C, 71.21; H, 6.90. Found: C, 70.96; H, 6.83.

EXAMPLE 25

4-[4-(6,7-Dihydroxy-2-naphthalenyl)butoxy]-2-hydroxy-3propylbenzoic acid

To a suspension of 3.3 g (7.6 mmole) of 2-hydroxy-4-[4-(6,7-dimethoxy-2-naphthalenyl)butoxy-3-propylbenzoic acid in 150 mL of methylene chloride cooled at −70° C. was added 25 mL (25 mmole) of 1M boron tribromide in methylene chloride. The mixture was stirred at −70° C. for 30 minutes and then kept at −20° C. for 5 hours. Workup as in Example 15 and recrystallization from ether-methylene chloride gave 1.85 g (59% yield), mp 173°–175° C., of 4-[4-(6,7-dihydroxy-2naphthalenyl)butoxy]-2-hydroxy-3-propyl-benzoic acid.

Anal. Calcd. for $C_{24}H_{44}O_6$: C, 70.23; H, 6.38. Found: C, 70.03; H, 6.35.

EXAMPLE 26

2-hydroxy-4-[4-[6.7-bis(phenylmethoxy)-2-naphthalenyl]butoxy]-3-propylbenzoic acid phenylmethyl ester A mixture of 5.0 g (11.6 mmole) of 2-(4-chlorobutyl)-6,7bis(phenylmethoxy)naphthalene, 3.3 g (11.6 mmole) of 2,4-dihydroxy-3-propylbenzoic acid phenylmethyl ester, 3.3 g (23.2 mmole) of potassium carbonate and 1.8 g (11.6 mmole) of sodium iodide in 70 mL of acetone-20 mL of dimethylformamide was stirred at reflux for 64 hours. Workup as in Example 16 and purification by HPLC using 9% ethyl acetate-hexane, followed by recrystallization from ether-hexane, gave 6.2 g (79% yield), mp 87°–89° C., of 2-hydroxy-4-[4-[6,7-bis(phenylmethoxy)-2-naphthalenyl]butoxy]-3-propylbenzoic acid phenylmethyl ester.

Anal. Calcd. for $C_{45}H_{44}O_6$: C, 79.39; H, 6.51. Found: C, 79.56; H, 6.50.

EXAMPLE 27

4-[4-(6,7-Dihydroxy-2-naphthalenyl)butoxy]-2-hydroxy-3-propylbenzoic acid

A mixture of 6.2 g of 2-hydroxy-4-[4-[6,7-bis(phenylmethoxy)-2-naphthalenyl]butoxy]-3-propylbenzoic acid phenylmethyl ester and 1.0 g of 10% palladium on carbon in 200 mL of tetrahydrofuran was shaken in a hydrogen atmosphere for 8 hours. Workup as in Example 17 and recrystallization from ether-methylene chloride gave 2.75 g (73% yield), mp 176°–177° C., of 4-[4-(6,7-dihydroxy-2-naphthalenyl)butoxy]-2-hydroxy-3-propylbenzoic acid.

EXAMPLE 28

4-[6-[6,7-bis(Phenylmethoxy)-2-naphthalenyl]hexyloxy]benzoic acid methyl ester

A mixture of 3.3 g (6.55 mmole) of 2-(6-bromohexyl)-6,7-bis(phenylmethoxy)naphthalene, 1.0 g (6.55 mmole) of 4-hydroxybenzoic acid methyl ester, 1.8 g (13.1 mmole) of potassium carbonate and 1.0 g (6.55 mmole) of sodium iodide in 50 mL of acetone-5mL of dimethylformamide was stirred at reflux for 28 hours. Workup as in Example 16 and recrystallization from methylene chloride-ether gave 3.3 g (88% yield), mp 121°–125° C., of 4-[6-[6,7-bis(phenylmethoxy)-2-naphthalenyl]hexyloxy]benzoic acid methyl ester.

Anal. Calcd. for $C_{38}H_{38}O_5$: C, 79.42; H, 6.66. Found: C, 79.44; H, 6.43.

EXAMPLE 29

4-[6-[6,7-bis(Phenylmethoxy)-2-naphthalenyl]hexyloxy]benzoic acid

A solution of 3.3 g of 4-[6-[6,7-bis(phenylmethoxy)-2-naphthalenyl]hexyloxy]benzoic acid methyl ester in 100 mL of methanol, 60 mL of dioxane and 3.8 mL of 1N sodium hydroxide was stirred at reflux for 24 hours. Workup as in Example 14 gave 3.1 g (96% yield), mp 153°–155° C., of 4-[6-[6,7-bis(phenylmethoxy)-2-naphthalenyl]hexyloxy]benzoic acid.

Anal. Calcd. for $C_{37}H_{36}O_5$: C, 79.26; H, 6.47. Found: C, 79.47; H, 6.58.

EXAMPLE 30

4-[6-(6,7-Dihydroxy-2-naphthalenyl)hexyloxy]benzoic acid

A mixture of 3.0 g of 4-[6-[6,7-bis(phenylmethoxy)-2-naphthalenyl-hexyloxy]benzoic acid and 0.6 g of 10% palladium on carbon in 200 mL of tetrahydrofuran was shaken in a hydrogen atmosphere for 17 hours. Workup as in Example 17 and recrystallization from acetone-hexane gave 1.8 g (86% yield), mp 160°–162° C., of 4-[6-(6,7-dihydroxy-2-naphthalenyl)hexyloxy]benzoic acid.

Anal. Calcd. for $C_{23}H_{24}O_5$: C, 72.61; H, 6.36. Found: C, 72.50; H, 6.36.

EXAMPLE 31

2-Hydroxy-4-[3-(6,7-dimethoxy-2-naphthalenyl)-propoxy]-3propylbenzoic acid phenylmethyl ester A mixture of 3.4 g (0.0128 mmole) of 2-(3-chloropropyl)-6,7dimethoxynaphthalene, 3.7 g (0.0128 mmole) of 2,4-dihydroxy-3propylbenzoic acid phenylmethyl ester, 3.6 g (0.0257 mole) of potassium carbonate and 1.9 g (0.0128 mole) of sodium iodide in 50 mL of acetone-25 mL of dimethylformamide was stirred at reflux for 23 hours. Workup as in Example 16 and purification by HPLC using 17% ethyl acetate-hexane gave 4.97 g (75% yield), mp 94°–96° C., of 2-hydroxy-4-[3-(6,7-dimethoxy-2-naphthalenyl)propoxy]-3-propylbenzoic acid phenylmethyl ester.

Anal. Calcd. for $C_{32}H_{34}O_6$: C, 74.69; H, 6.66. Found: C, 74.86; H, 6.78.

EXAMPLE 32

2-Hydroxy-4-[3-(6.7-dimethoxy-2-naphthalenyl)-propoxy]-3propylbenzoic acid

A mixture of 4.95 g of 2-hydroxy-4-[3-(6,7-dimethoxy-2-naphthalenyl)propoxy]-3-propylbenzoic acid phenylmethyl ester and 0.5 g of 10% palladium on carbon in 200 mL of tetrahydrofuran was shaken in a hydrogen atmosphere for 3 hours. Workup as in Example 17 gave 4.1 g, mp 165°–168° C., of 2-hydroxy-4-[3-(6,7-dimethoxy-2-naphthalenyl)propoxy]-3-propylbenzoic acid.

Anal. Calcd. for $C_{25}H_{28}O_6$: C, 70.74; H, 6.65. Found: C, 70.58; H, 6.67.

EXAMPLE 33

-[3-(6,7-Dihydroxy-2-naphthalenyl)propoxy]-2-hydroxy-3propylbenzoic acid

To a suspension of 4.05 g of 2-hydroxy-4-[3-(6,7-dimethoxynaphthalenyl)propoxy]-3-propylbenzoic acid in 250 mL of methylene chloride cooled at −70° C. was added 33 mL of 1M boron tribromide in methylene chloride. The mixture was stirred at −70° C. for 30 minutes and then kept at −20° C. for 19 hours. Workup as in Example 15 and recrystallization from ether-methylene chloride gave 2.98 g (79% yield), mp 218°–220° C., of 4-[3-(6,7-dihydroxy-2-naphthalenyl)-propoxy]-2-hydroxy3-propylbenzoic acid.

Anal. Calcd. for $C_{23}H_{24}O_6$: C, 69.68; H, 6.10. Found: C, 69.22; H, 6.14.

EXAMPLE 34

2-Hydroxy-4-[2-(6,7-dimethoxy-2-naphthalenyl)ethoxy]-3propylbenzoic acid phenylmethyl ester To 5.03 g (0.0216 mole) of 2-(2-hydroxyethyl)-6,7dimethoxynaphthalene in 75 mL of methylene chloride, cooled in an ice bath, was added 6 mL (0.043 mole) of triethylamine followed by 2.2 mL (0.028 mole) of methanesulfonyl chloride. The reaction mixture was stirred at 3° C. for 1 hour and then was washed with 1N hydrochloric acid, 5% sodium bicarbonate solution. The organic layer was dried and concentrated under reduced pressure to give 2-(2-methanesulfonyloxyethyl)-6,7-dimethoxynaphthalene, which was used without purification. A mixture of this mesylate, 5.5 g (0.019 mole) of 2,4-dihydroxy-3-propylbenzoic acid phenylmethyl ester, 0.7 mL of TDA-1 and 5.4 g (0.039 mole) of potassium carbonate in 180 mL of toluene was stirred at reflux for 18 hours. The reaction mixture was washed with water, dried and concentrated under reduced pressure to a solid which was recrystallized from methylene chloride-methanol-water, to give 8.6g (89% yield), mp 112°–113° C., of 2-hydroxy-4-[2-(6,7-dimethoxy-2-naphthalenyl)ethoxy]-3-propylbenzoic acid phenylmethyl ester.

Anal. calcd for $C_{31}H_{32}O_6$: C, 74.38; H, 6.44. Found: C, 74.51; H, 6.66.

EXAMPLE 35

2-Hydroxy-4-2-(6,7-dimethoxy-2-naphthalenyl)ethoxy]-3propylbenzoic acid

A mixture of 8.6 g of 2-hydroxy-4-[2,(6,7-dimethoxy-2naphthalenyl)ethoxy]-3-propylbenzoic acid phenylmethyl ester and 1.0 g of 10% palladium on carbon in 150 mL of ethyl acetate- 100 mL of tetrahydrofuran was shaken under 54 psi of hydrogen pressure in a Parr hydrogenator for 4 hours. Workup as in Example 17 and recrystallization from ethyl acetate hexane gave 6.4 g (92% yield), mp 209−210° C., of 2-hydroxy-4-[2-(6,7-dimethoxy-2-naphthalenyl)e-thoxy]-3-propylbenzoic] acid.

EXAMPLE 36

4-[2-(6,7-Dihydroxy-2-naphthalenyl)ethoxy]-2-hydroxy-3propylbenzoic acid

To a suspension of 6.4 g of 2-hydroxy-4-[2-(6,7-dimethoxy-2-naphthalenyl)ethoxy]-3-propylbenzoic acid in 400 mL of methylene chloride cooled at −70° C. was added 55 mL of 1M boron tribromide in methylene chloride. The mixture was stirred at −70° C. for 45 minutes and then kept at −20° C. for 18 hours. Workup as in Example 15 and recrystallization from ethanol-water gave 0.33 g, mp 216°–218° C., of 4-[2-(6,7-dihydroxy-2-naphthalenyl) ethoxy]-2-hydroxy-3-propylbenzoic acid.

Anal. Calcd for $C_{22}H_{22}O_6$: C, 69.10; H, 5.80. Found: C, 68.87; H, 5.83

EXAMPLE 37

2-Hydroxy-4-[6-[6,7-bis(phenylmethoxy)-2-naphthalenyl]hexyloxy]benzoic acid methyl ester A mixture of 3.3 g (6.55 mmole) of 2-(6-bromohexyl)-6,7-bis (phenylmethoxy) naphthalene, 1.1 g (6.55 mmole) of 2,4-dihydroxybenzoic acid methyl ester, 1.8 g (13.1 mmole) of potassium carbonate and 1.0 g (6.55 mmole) of sodium iodide in 50 mL of acetone-5-mL of dimethyl formamide was stirred at reflux for 28 hours. Workup as in Example 16 and recrystallization from methylene chloride-methanol gave 3.2 g (84% yield), mp 129°–131° C., of 2-hydroxy-4-[6-[6,7-bis (phenylmethoxy)-2-naphthalenyl]hexyloxy]benzoic acid methyl ester.

Anal. Calcd for $C_{38}H_{38}O_6$: C, 77.27; H, 6.48. Found: C, 77.17; H, 6.45.

EXAMPLE 38

2-Hydroxy-4-[6,7-bis(phenylmethoxy)-2-naphthalenyl]-hexyloxy]benzoic acid

A solution of 3.2 g (5.46 mmole) of 2-hydroxy-4-[6-[6,7-bis (phenylmethoxy)-2-naphthalenyl]hexyloxy]benzoic acid methyl ester in 100 mL of methanol and 60 mL of dioxane and 3.6 mL (22 mmole) of 6N sodium hydroxide was stirred at reflux for 69 hours. Workup as in Example 14 gave 3.1 g, mp 149°–153° C., of 2-hydroxy- 4-[6-[6,7-bis(phenylmethoxy)-2-naphthalenyl]hexyloxy]benzoic acid.

Anal. Calcd for $C_{37}H_{36}O_6$: C, 77.06; H, 6.29. Found: C, 77.13 H, 6.29.

EXAMPLE 39

4-[6-(6,7-Dihydroxy-2-naphthalenyl)hexyloxy]-2-hydroxybenzoic acid

A mixture of 3.1 g of 2-hydroxy-4-[6-[6,7-bis(phenylmethoxy)-2-naphthalenyl]hexyloxy]benzoic acid and 0.6 g of 10% palladium on carbon in 200 mL of tetrahydrofuran was shaken in a hydrogen atmosphere for 17 hours. Workup as in Example 17 and recrystallization from ether-methylene chloride gave 1.5 g (70% yield), mp 190°–192° C., of 4-[6-(6,7-dihydroxy-2naphthalenyl)hexyloxy]-2-hydroxy-benzoic acid.

Anal. Calcd for $C_{23}H_{24}O_6$: C, 69.68; H, 6.10. Found: C, 69.06; H, 5.95.

EXAMPLE 40

2-Hydroxy-4-[[5-(6,7-dimethoxy-2-naphthalenyl)-5-oxopentyl]oxy]-3-propylbenzoic acid phenylmethyl ester A mixture of 15.0 g (42.% mmole) of 5-bromo 1-(6,7-dimethoxy-2-naphthalenyl)-1-pentanone, 12.3 g (42.7 mmole) of 2,4-dihydroxy-3-propylbenzoic acid phenylmethyl ester, 11.8 g (85.4 mmole) of potassium carbonate and 6.4 g (42.7 mmole) of sodium iodide in 175 mL of acetone-40 mL of dimethylformamide was stirred at reflux for 72 hours. Workup as in Example 16 and recrystallization from methylene chloride-ether gave 17.6 g (74% yield), mp 126°–127° C., of 2-hydroxy-4-[[5,(6,7-dimethoxy-2-naphthalenyl)-5-oxopentyl]oxy]-3-propylbenzoic acid phenylmethyl ester.

Anal. Calcd for $C_{23}H_{24}O_6$: C, 73.36; H, 6.52. Found: C, 73.33, H, 6.56.

EXAMPLE 41

2-Hydroxy-4-[[5-(6,7-dimethoxy-2-naphthalenyl)-5-oxopentyl]oxy]-3-propylbenzoic acid A solution of 15.65 g (28 mmole) of 2-hydroxy-4-[[5-(6,7-dimethoxy-2-naphthalenyl)-5-oxopentyl]oxy]-3-propylbenzoic acid phenylmethyl ester and 38 mL (114 mmole) of 3N sodium hydroxide in 400 mL of methanol and 125 mL of dioxane was stirred at reflux for 8 hours. Workup as in Example 14 and recrystallization from acetone-hexane gave 12.4 g (96% yield), mp 177°–178° C., of 2-hydroxy-4-[[5-(6,7-dimethoxy-2-naphthalenyl)-5-oxopentyl]oxy]-3-propylbenzoic acid.

Anal. Calcd for $C_{25}H_{26}O_6$: C, 69.51; H, 6.48. Found: C, 69.20; H, 6.49.

EXAMPLE 42

4-[[5-(6,7-Dihydroxy-2-naphthalenyl)-5-oxopentyl]oxy]-2-hydroxy-3-propylbenzoic acid To a suspension of 5.0 g (10.7 mmole) of 2-hydroxy-4-[[5-(6,7-dimethoxy-2-naphthalenyl)-5-oxopentyl]oxy]-3-propylbenzoic acid in 350 mL of methylene chloride, cooled at −70° C., was added 39 mL (39 mmole) of 1M boron tribromide in methylene chloride. The mixture was stirred at −70° C. for 30 minutes and then was kept at −20° C. for 8 hours. Workup as in Example 15 and recrystallization from acetone-chloroform gave 2.6 g (56% yield), mp 213°–214° C., of 4-[[5-(6,7-dihydroxy-2-naphthalenyl)-5-oxopentyl]oxy]-2-hydroxy-3-propylbenzoic acid.

Anal. Calcd for $C_{25}H_{26}O_7$: C, 68.48; H, 5.98. Found: 68.30; H, 5.97.

EXAMPLE 43

2-Hydroxy-4-[5-(6,7-dimethoxy-2-naphthalenyl)pentyloxy]-3-propylbenzoic acid

A mixture of 7.3 g of 2-hydroxy-4-[[5-(6,7-dimethoxy-2-naphthalenyl)-5-oxopentyl]oxy]-3-propylbenzoic acid and 2.0 g of 10% palladium on carbon in 150 mL of tetrahydrofuran and 10 mL of acetic acid and 2 drops of concentrated sulfuric acid was shaken under 54 psi of hydrogen pressure in a Parr hydrogenator for 6 hours. Workup as in Example 6 and recrystallization from methylene chloride-hexane gave 6.2 g (88% yield), mp 135°–137° C., of 2-hydroxy-4-[5-(6,7-dimethoxy-2naphthalenyl)pentyloxy]–3-propylbenzoic acid.

Anal. Calcd. for $C_{27}H_{32}O_6$: C, 71.66; H, 7.13. Found: C, 71.50; H, 7.27.

EXAMPLE 44

4-[5-(6,7-Dihydroxy-2-naphthalenyl)pentyloxy]-2-hydroxy-3-propylbenzoic acid

To a suspension of 6.18 g (13.7 mmole) of 2-hydroxy-4-[5(6,7-dimethoxy-2-naphthalenyl)pentyloxy]-3-propylbenzoic acid in 400 mL of methylene chloride, cooled at −70° C., was added 50 mL (50 mmole) of 1M boron tribromide in methylene chloride. The mixture was stirred at −70° C. for 30 minutes and then was kept at −20° C. for 18 hours. Workup as in Example 15 and recrystallization from ether-methylene chloride gave 3.0 g (52% yield), mp 165°–167° C., of 4-[5-(6,7-dihydroxy-2-naphthalenyl)pentyloxy]−2-hydroxy-3-propylbenzoic acid.

Anal. Calcd. for $C_{25}H_{28}O_6$: C, 70.74; H, 6.65. Found: C, 70.45; H, 6.73.

EXAMPLE 45

4-[4-(5,8-Dichloro-6,7-dimethoxy-2-naphthalenyl)butoxy]-2-hydroxy-3-propylbenzoic acid phenylmethyl ester A mixture of 3.29 g (9.46 mmole) of 1,4-dichloro-6(4-chlorobutyl)-2,3-dimethoxynaphthalene, 2.70 g (9.46 mmole) of 2,4-dihydroxy-3-propylbenzoic acid phenylmethyl ester, 2.6 g (18.9 mmole) of potassium carbonate and 1.4 g (9.46 mmole) of sodium iodide in 80 mL of acetone and 15 mL of dimethylformamide was stirred at reflux for 36 hours. Workup as in Example 16 and purification by HPLC using 5% ethyl acetate-hexane gave 4.28 g (76% yield), mp 66°–68° C., of 4-[4-(5,8-dichloro-6,7-dimethoxy-2-naphthalenyl)butoxy]-2-hydroxy-3-propylbenzoic acid phenylmethyl ester.

Anal. Calcd for $C_{33}H_{34}Cl_2O_6$: C, 66.33; H, 5.74; Cl, 11.87. Found: C, 66.08; H, 5.76; Cl, 11.68.

EXAMPLE 46

4-[4-(5,8-Dichloro-6,7-dimethoxy-2-naphthalenyl)butoxy]-2-hydroxy-3-propylbenzoic acid A solution of 4.06 g (6.8 mmole) of 4-[4-(5,8-dichloro-6,7-dimethoxy-2-naphthalenyl)butoxy]-2-hydroxy-3-propylbenzoic acid phenylmethyl ester and 9 mL (27 mmole) of 3N sodium hydroxide in 150 mL of methanol amd 50 mL of dioxane was heated at reflux for 4 hours. Workup as in Example 14 and recrystallization from acetone-hexane gave 3.11 g (90% yield), mp 181°–182° C., of 4-[4-(5,8-dichloro-6,7-dimethoxy-2-naphthalenyl)butoxy]-2-hydroxy-3-propylbenzoic acid.

Anal. Calcd. for $C_{26}H_{Cl2}O_6$: C, 61.55; H, 5.56; Cl, 13.97. Found: C, 61.43; H, 5.56; Cl, 13.88.

EXAMPLE 47

4-[4-(5,8-Dichloro-6,7-dihydroxy-2-naphthalenyl)-butoxy]-2-hydroxy-3-propylbenzoic acid To a suspension of 3.17 g (6.25 mmole) of 4-[4-(5,8-dichloro-6,7-dimethoxy-2-naphthalenyl)butoxy]-2-hydroxy-3 propylbenzoic acid in 350 mL of methylene chloride, cooled at −70° C., was added 22 mL (22 mmole) of 1M boron tribromide in methylene chloride. The mixture was stirred at −70° C. for 30 minutes and then was kept at −20° C. for 20 hours. Workup as in Example 15 and recrystallization from ether-hexane gave 1.50 g (50% yield), mp 201°–203° C., of 4-[4-(5,8-dichloro-6,7-dihydroxy-2-naphthalenyl)butoxy]-2-hydroxy-3-propylbenzoic acid.

Anal. Calcd for $C_{24}H_{24}Cl_2O_6$: C, 60.14; H, 5.05; Cl, 14.79. Found: C, 59.94; H, 4.96; Cl, 14.40.

EXAMPLE 48

TABLET FORMULATION (Wet Granulation)

| | | mg/tablet | | |
|---|---|---|---|---|
| Item | Ingredient | 100 mg | 500 mg | 1000 mg |
| 1. | 4-[4-(6,7-Dihydroxy-2-naphthalenyl)butoxy]-2-hydroxy-3-propylbenzoic acid | 100 | 500 | 1000 |
| 2. | Lactose | 132 | — | — |
| 3. | Pregelatinized starch | 16 | 30 | 50 |
| 4. | Modified starch | 30 | 40 | 50 |
| 5. | Magnesium stearate | 2 | 6 | 8 |
| | TOTAL | 280 | 576 | 1108 |

Manufacturing Procedure:
1. Mix items 1, 2, 3 and 4 and granulate with water.
2. Dry the granulation at 50° C.
3. Pass the granulation through suitable milling equipment.
4. Add item 5 and mix for three minutes; compress on a suitable press.

EXAMPLE 49

CAPSULE FORMULATION

| | | mg/capsule | | | |
|---|---|---|---|---|---|
| Item | Ingredient | | | | |
| 1. | 4-[4-(6,7-Dihydroxy-2-naphthalenyl)butoxy]-2-hydroxy-3-propylbenzoic acid | 25 | 50 | 100 | 500 |
| 2. | Lactose hydrous | 143 | 168 | 148 | — |
| 3. | Corn starch | 20 | 20 | 40 | 70 |
| 4. | Talc | 10 | 10 | 10 | 25 |
| 5. | Magnesium stearate | 2 | 2 | 2 | 2 |
| | TOTAL | 200 | 250 | 300 | 600 |

Manufacturing Procedure:
1. Mix items 1, 2 and 3 in a suitable mixer for 30 minutes.
2. Add items 4 and 5 and mix for 3 minutes.
3. Fill into suitable capsules.

EXAMPLE 50

WET GRANULATION FORMULATION

| Item | Ingredient | mg/tablet | |
|---|---|---|---|
| 1. | 4-[4-(6,7-Dihydroxy-2-naphthalenyl)butoxy]-2-hydroxy-3-propylbenzoic acid | 25 | 50 |
| 2. | Polyvinyl pyrrolidone | 5 | 10 |
| 3. | Lactose, anhydrous DTG | 133 | 142 |
| 4. | Microcrystalline cellulose | 25 | 30 |
| 5. | Modified starch | 10 | 15 |
| 6. | Magnesium stearate | 2 | 3 |
| | TOTAL | 200 | 250 |

Manufacturing Procedure:
1. Dissolve item 2 in water.
2. Mix items 1, 3, 4 and 5 in a suitable mixer and granulate with solution from step 1.
3. Dry overnight at 45° C., screen through #20 mesh, and add item 6 and mix. Compress on a suitable press.

EXAMPLE 51

SOFT GELATIN CAPSULE FORMULATION

| Item | Ingredient | mg/capsule | |
|---|---|---|---|
| 1. | 4-[4-(6,7-Dihydroxy-2-naphthalenyl)butoxy]-2-hydroxy-3-propylbenzoic acid | 50 | 150 |
| 2. | Polyethylene glycol 400 | 325 | 550 |
| 3. | Medium chain monoglycerides | 100 | 150 |
| 4. | Polysorbate 80 | 25 | 50 |
| | TOTAL | 500 | 1000 |

Manufacturing Procedure:
1. Dissolve item 1 in item 2.
2. Add item 3 and mix well.
3. Add item 4 and mix well until dissolved.
4. Fill into soft gelatin capsules.

EXAMPLE 52

BEADLET FORMULATION (ENTERIC)

| Item | Beadlet/Ingredient | mg/capsule | | |
|---|---|---|---|---|
| 1. | 4-[4-(6,7-Dihydroxy-2-naphthalenyl)butoxy]-2-hydroxy-3-propylbenzoic acid | 25 | 100 | 250 |
| 2. | Microcrystalline cellulose | 100 | 200 | 250 |
| 3. | Polyvinyl pyrrolidone K-90 | 10 | 20 | 30 |
| | TOTAL | 135 | 320 | 530 |

Procedure:
1. Mix item 1 with item 2 and granulate with a solution of item 3.
2. Pass the granulation through an extruder and marumarizer to obtain uniform beads.
3. Coat the beads with an enteric polymer such as polyvinyl acetate phthalate, hydroxypropyl methylcellulose phthalate, cellulose acetate phthalate, or an acrylic polymer.
4. Fill into capsules at the appropriate fill weight.

BEADLET FORMULATION (ENTERIC) II

Starting with non-pareil seeds, deposit on the seeds with an appropriate polymer, such as polyvinyl pyrrolidone, hydroxypropyl cellulose, hydroxypropyl methylcellulose or the like. Dry the seeds and apply an enteric membrane such as polyvinyl acetate phthlate, hydroxypropyl methylcellulose phthlate, cellulose acetate phthlate and/or an acrylic Polymer. Determine the concentration of the drug per gram of Beadlet and fill into capsules.

Exemplary of still other compounds of the invention which can be prepared by procedures similar to those described in the foregoing Examples are the following:

4-[[5-(6,7-dihydroxy-2-naphthalenyl)-5-oxopentyl]oxy]-2-hydroxy-propylbenzoic acid 4-[[7-(6,7-dihydroxy-2-naphthalenyl)-7-oxoheptyl]oxy]-2-hydroxy-propylbenzoic acid 4-[[8-(6,7-dihydroxy-2-naphthalenyl)-8-oxooctyl]oxy]-2-hydroxy-propylbenzoic acid
4-[[9-(6,7-dihydroxy-2-naphthalenyl)-9-oxononyl]oxy]-2-hydroxy-3-propylbenzoic acid
4-[[6-(6,7-dihydroxy-2-naphthalenyl)-6-oxohexyl]oxy]-2-hydroxybenzoic acid
4-[[6-(6,7-dihydroxy-2-naphthalenyl)-6-oxohexyl]oxy]-3-propylbenzoic acid
4-[[6-(6,7-dihydroxy-2-naphthalenyl-6-oxohexyl]oxy]benzoic acid
4-[[6-(6,7-diacetyloxy-2-naphthalenyl-6-oxohexyl]oxy]-2-hydroxy-propylbenzoic acid
4-[[6-(5,8-dichloro-6,7-dihydroxy-2-naphthalenyl)-6-oxohexyl]oxy]-2-hydroxy-3-propylbenzoic acid
4-[7-(6,7-dihydroxy-2-naphthalenyl)heptyloxy]-2-hydroxy-3-propylbenzoic acid
4-[8-(6,7-dihydroxy-2-naphthalenyl)octyloxy]-2-hydroxy-3-propylbenzoic acid
4-[9-(6,7-dihydroxy-2-naphthalenyl)nonyloxy]-2-hydroxy-3-propylbenzoic acid
4-[10-(6,7-dihydroxy-2-naphthalenyl)decyloxy-2-hydroxy-3-propylbenzoic acid
4-[6-(5,8-dichloro-6,7-dihydroxy-2-naphthalenyl)hexyloxy]-2-hydroxy-3-propylbenzoic acid
4-[4-(5,8-dichloro-6,7-dihydroxy-2-naphthalenyl)-butoxy]-2-hydroxybenzoic acid
4-[4-(5,8-dichloro-6,7-dihydroxy-2-naphthalenyl)-butoxy]-2-hydroxy -3-propylbenzoic acid ethyl ester
4-[4-(6,7-dihydroxy-2-naphthalenyl)butoxy]-2-hydroxybenzoic acid
4-[4-(6,7-dihydroxy-2-naphthalenyl)butoxy]-benzoic acid
4-[4-(6,7-dihydroxy-2-naphthalenyl)butoxy]-3-propylbenzoic acid
4-[4-(6,7-diacetyloxy-2-naphthalenyl)butoxy]-2-hydroxy-3-propylbenzoic acid
4-[4-(6,7-dihydroxy-2-naphthalenyl)butoxy]-2-hydroxy-3-propylbenzoic acid ethyl ester
4-[6-(6,7-dihydroxy-2-naphthalenyl)hexyloxy]-2-hydroxy-3-propylbenzoic acid ethyl ester

We claim:

1. A compound of the formula

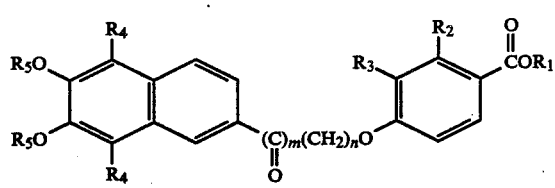

in which $R_1$ is hydrogen, lower alkyl or benzyl, $R_2$ is hydrogen, Hydroxy or lower alkanoyloxy, $R_3$ is hydrogen or lower alkyl, $R_4$ is hydrogen or halogen, $R_5$ is hydrogen, acyl, methyl or benzyl, m is 0 or 1, and n is an integer from 2 to 10, or a salt thereof with a pharmaceutically acceptable base when $R_1$ is hydrogen.

2. A compound in accordance with claim 1, in which $R_1$ is hydrogen, $R_2$ is hydroxy, $R_3$ is lower alkyl, $R_4$ and $R_5$ are hydrogen, n is 2–10, and m is 0 or 1.

3. A compound in accordance with claim 2, in which $R_1$ is hydrogen, $R_2$ is hydroxy, $R_3$ is propyl, $R_4$ and $R_5$ are hydrogen, n is 4–6 and m is 0.

4. A compound in accordance with claim 1, which is 4-[6-(6,7-dihydroxy-2-naphthalenyl)hexyloxy]-2-Hydroxy-3-propylbenzoic acid.

5. A compound in accordance with claim 1, which is 4-[5-(6,7-dihydroxy-2-naphthalenyl)pentyloxy]-2-hydroxy-3-propylbenzoic acid.

6. A compound in accordance with claim 1, which is 4-[4-(6,7-dihydroxy-2-naphthalenyl)butoxy]-2-hydroxy-3-propylbenzoic acid.

7. A compound in accordance with claim 1, which is 4-[3-(6,7-dihydroxy-2-naphthalenyl)propoxy]-2-hydroxy-3-propylbenzoic acid.

8. A compound in accordance with claim 1, which is 4-[2-(6,7-dihydroxy-2-naphthalenyl)ethoxy]-2-hydroxy-3-propylbenzoic acid.

9. A compound in accordance with claim 1, which is 4-[6-(6,7-dihydroxy-2-naphthalenyl)hexyloxy]-benzoic acid.

10. A compound in accordance with claim 1, which is 4-[6-(6,7-dihydroxy-2-naphthalenyl)hexyloxy]-2-hydroxybenzoic acid.

11. A compound in accordance with claim 1, which is 4-[[6-(6,7-dihydroxy-2-naphthalenyl)-6-oxohexyl]oxy]-2-hydroxypropylbenzoic acid.

12. A compound in accordance with claim 1, which is 4-[[5-(6,7-dihydroxy-2-naphthalenyl)-5-oxopentyl]oxy]-2-hydroxy-3-propylbenzoic acid.

13. A compound in accordance with claim 1, which is 4-[[6-(6,7-dihydroxy-2-naphthalenyl)-6-oxohexyl]oxy]-2-hydroxy-3-propylbenzoic acid.

14. A compound in accordance with claim 1, which is 4-[4-(5,8-dichloro-6,7-dihydroxy-2-naphthalenyl)butoxy]-2-hydroxy-3-propylbenzoic acid.

15. A pharmaceutical composition comprising an effective amount of a compound of the formula

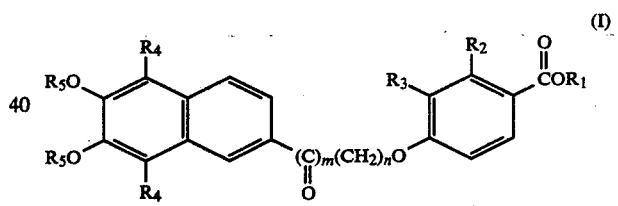

in which $R_1$ is hydrogen, lower alkyl or benzyl, $R_2$ is hydrogen, hydroxy or lower alkanoyloxy, $R_3$ is hydrogen or lower alkyl, $R_4$ is hydrogen or halogen, $R_5$ is hydrogen or acyl, m is 0 or 1, and n is an integer from 2 to 10, or a salt thereof with a pharmaceutically acceptable base when $R_1$ is hydrogen, and an inert carrier material.

16. A pharmaceutical composition in accordance with claim 15, in which $R_1$ is hydrogen, $R_2$ is hydroxy, $R_3$ is lower alkyl, $R_4$ and $R_5$ are hydrogen, n is 2–10, and m is 0 or 1.

17. A pharmaceutical composition in accordance with claim 16, in which $R_1$ is hydrogen, $R_2$ is hydroxy. $R_3$ is propyl. $R_4$ and $R_5$ are hydrogen, n is 4–6, and m is 0.

18. A Pharmaceutical composition in accordance with claim 15, in which the compound of formula I is 4-[4-(6,7-dihydroxy-2naphthalenyl)butoxy]-2-hydroxy-3-propylbenzoic acid.

19. A method of inhibiting $\Delta^5$-lipoxygenase in a host requiring such treatment, which comprises administering an effective amount of a compound of the formula

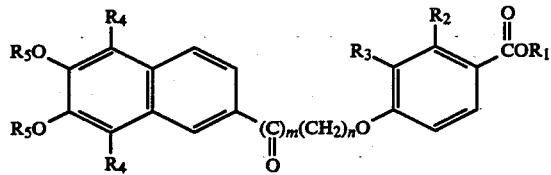

in which R is hydrogen, lower alkyl or benzyl, $R_2$ is hydrogen, hydroxy or lower alkanoyloxy, $R_3$ is hydrogen or lower alkyl, $R_4$ is hydrogen or halogen, $R_5$ is hydrogen or acyl, m is 0 or 1, and n is an integer from 2 to 10, or a salt thereof with a pharmaceutically acceptable base when $R_1$ is hydrogen.

20. A method in accordance with claim 19 in which $R_1$ is hydrogen, R is hydroxy, $R_3$ is lower alkyl, $R_4$ and $R_5$ are hydrogen, n is 2–10, and m is O or 1.

21. A method in accordance with claim 20, in which $R_1$ is hydrogen, $R_2$ is hydroxy, $R_3$ is propyl, $R_4$ and $R_5$ are hydrogen, n is 4–6, and m is 0.

22. A method in accordance with claim 19, in which the compound of formula I is 4-[4-(6,7-dihydroxy-2-naphthalenyl)butoxy]-2-hydroxy-3-propylbenzoic acid.

* * * * *